United States Patent [19]
Smith et al.

[11] Patent Number: 5,374,550
[45] Date of Patent: Dec. 20, 1994

[54] THYROID-DERIVED CHONDROCYTE-STIMULATING FACTOR

[75] Inventors: R. Lane Smith, Palo Alto; Deryk G. Jones, Menlo Park, both of Calif.

[73] Assignee: The Board of Trustees of the Leland Stanford Junior University, Stanford, Calif.

[21] Appl. No.: 152,224

[22] Filed: Nov. 12, 1993

Related U.S. Application Data

[62] Division of Ser. No. 654,965, Feb. 13, 1991, Pat. No. 5,284,830.

[51] Int. Cl.$^5$ ............................ A61F 2/08; C12N 5/08
[52] U.S. Cl. ...................... 435/240.23; 435/240.31; 623/13
[58] Field of Search ............... 514/2, 12, 21; 530/350, 530/399, 402, 837, 854; 424/422, 423, 568; 435/1, 240.23, 240.243, 240.31; 623/13, 14; 600/36

[56] References Cited

U.S. PATENT DOCUMENTS 4,356,261 10/1982 Kuettner ..................... 435/240.243
4,810,691 3/1989 Seyedin et al. .................... 514/2

OTHER PUBLICATIONS

McQuillan, D. J., et al., "Stimulation of proteoglycan biosynthesis by serum and insulin-like growth factor-I in cultured bovine cartilage" Biochem. J. (1986) 240:423-430.
Ross, R., et al., "The biology of platelet-derived growth factor" Cell (1986) 46:155-169.
Smith, R. L., et al., "Growth hormone stimulates insulin-like growth factor I actions on adult articular chondrocytes" J. Orthoped. Res. (1989) 7:198-207.
Tucker, R. F., et al., "Comparison of intra-and extracellular transforming growth factors from nontransformed and chemically transformed mouse embryo cells" Cancer Res. (1983) 43:1581-1586.
Jones, D. G., et al., "Stimulation of adult chondrocyte metabolism by a thyroid-derived factor" J. Orthoped. Res. (1990) 8:227-233.
Lobb, R. R., et al., "Purification of heparin-binding growth factors" Anal. Biochem. (1986) 154:1-14.
Harris, E. L. V., et al., eds., Protein Purification Methods, (1989) IRL Press, New York, pp. 9-10 and 57-60.
Jones, D. G., et al., "Ammonium sulfate precipitation of thyroid-derived cartilage stimulating factor" Clin. Res. (1989) 37(1):224A.
Malemud, C. J., et al., "The effect of chondrocyte growth factor on membrane transport by articular chondrocytes in monolayer culture" Connect. Tiss. Res. (1978) 6:1-9.
Cohen, S., et al., "Interaction of epidermal growth factor (EGF) with cultured fibroblasts" Adv. Metab. Disord. (1975) 8:265-284.
Froesch, E. R., et al., "Actions of insulin-like growth factors" Ann. Rev. Physiol. (1985) 47:443-467.
Gospodarowicz, D., et al., "Structural characterization and biological functions of fibroblast growth factor" Endocrin. Rev. (1987) 8(2):95-114.

Primary Examiner—Jeffrey E. Russel
Attorney, Agent, or Firm—Morrison & Foerster

[57] ABSTRACT

Thyroid-derived chondrocyte stimulating factor (TDCSF) is a high molecular weight complex (greater than 500 kd) of proteinaceous subunits which can be at least partially dissociated into active portions by 8M urea. TDCSF stimulates articular chondrocyte and synovial fibroblast growth under serum-free conditions. TDCSF is useful for the culture of chondrocytes and fibroblasts in vitro as a serum substitute; for developing cartilage implants in vitro; and for in vivo use in cartilage and bone defect repair and degenerative joint diseases. TDCSF is stabilized in the presence of reducing agents for disulfide bonds. Antibodies for and conjugates of TDCSF are also disclosed.

2 Claims, 3 Drawing Sheets

THYROID-DERIVED CHONDROCYTE-STIMULATING FACTOR

This application is a continuation, division of application Ser. No. 07/654,965 filed Feb. 13, 1991 now U.S. Pat. No. 5,284,830.

TECHNICAL FIELD

The invention relates to a factor useful for cartilage repair including in vitro stimulation of chondrocytes and synovial fibroblasts. More particularly, it concerns a factor which can be isolated from thyroid tissue which stimulates both synovial fibroblasts and chondrocytes under serum-free conditions and which is stabilized by reducing agents that reduce disulfides.

BACKGROUND AND RELATED ART

A number of factors are known that stimulate the growth of various cells under a variety of conditions. Most closely related to the factor disclosed herein in their activities with regard to the cells characterizing the bony and connective tissues are those which have a stimulatory effect on articular chondrocytes. These include transforming growth factor $\beta$ (TGF-$\beta$), platelet derived growth factor (PDGF), insulin-like growth factors types I and II (IGF-I and IGF-II), acidic and basic fibroblast growth factors (FGF) and epidermal derived growth factor (EGF). (Cohen, S., et al., *Adv Metab Disord* (1975) 8:265–284; Froesch, E. R., et al., *Ann Rev Physiol* (1985) 47:443–467; Gospodarowicz, D., et al., *Endocrine Reviews* (1987) 8:95–114; McQuillan, D. J., et al., *Biochem J* (1986) 240:423–430; Ross, R., et al., *Cell* (1986) 46:155–169; Smith, R. L., et al., *J Orthop Res* (1989) 7:198–207; Tucker, R. F., et al., *Cancer Res* (1983) 43:1581–1586.

The known thyroid hormones, 3,3',5'-triiodo-1,3-L-thyronine ($T_3$); thyroxine ($T_4$) and calcitonin are known to affect connective tissue metabolism. However, their effects are generally directed to immature cells. $T_3$ and $T_4$ are important for growth and maturation of the epithelial cartilage secondary ossification, and generalized skeletal development; calcitonin increases hypertrophy and maturation of embryonic and growth plate cartilage, but resting cartilage is unresponsive to calcitonin.

In a recent publication, applicants disclosed the presence of an activity in partially purified thyroid calcitonin which provided stimulation of adult articular chondrocyte proliferation and glycosaminoglycan synthesis under serum-free conditions—conditions wherein none of $T_3$, $T_4$ or calcitonin provide such stimulation. In this paper, Jones, D. G. and Smith, R. L., *J Orthoped Res* (1990) 8:227–233, the disclosure of which is incorporated herein by reference, the authors disclosed that this activity could be eluted from heparin-Sepharose at low salt concentration (0.5M NaCl)—conditions under which the fibroblast growth factors, known to stimulate articular chondrocyte proliferation under similar conditions, are not eluted from this support. Acidic FGF is eluted at 1M NaCl under comparable conditions and basic FGF is eluted at 1.6M NaCl under comparable conditions (Lobb, R. R., et al., *Anal Biochem* (1986) 154:1–14.) The nature of this activity was not further characterized.

It has now been found that the chondrocyte stimulating activity obtainable from thyroid tissue is associated with a complex of high molecular weight components which can be prepared in isolated and purified form. The invention herein thus provides a new factor for the stimulation of connective tissue growth.

DISCLOSURE OF THE INVENTION

The invention provides a complex of high molecular weight which can be at least partially dissociated by 8M urea into active subunits. Both the complex and the dissociated subunits stimulate chondrocyte and synovial fibroblast growth under serum-free conditions in vitro and can thus be used as a substitute for serum in the culture of these cells. Furthermore, the complex or its dissociated portions are useful in the in vitro development of implants for medical use, and are useful in vivo in the treatment of connective tissue conditions which require the enhancement of connective tissue growth and/or the integration of grafts or implants into bone or cartilage.

Thus, in one aspect, the invention is directed to a high molecular weight proteinaceous complex with the ability to stimulate chondrocyte or synovial fibroblast growth under serum-free conditions in vitro. The complex can be at least partially dissociated by 8M urea into portions of the complex which retain this activity but which are also of high molecular weight (>500 kd). The invention is also directed to these subunits. The complex and its subunits, collectively called thyroid-derived chondrocyte stimulating factor (TDCSF), are stabilized by reducing agents that are capable of reducing disulfide bonds, such as mercaptoethanol and dithiothreitol. They are (the factor is) inactivated by treatment with acetic acid for one hour at 4° C., and by treatment by trypsin. The complex and its subunits are also inactivated by heating to 100° C. for one hour but not by heating to 60° C. for one hour. The factor can be eluted from heparin-Sepharose at 0.5M NaCl.

In additional aspects, the invention is directed to pharmaceutical compositions, including implant compositions containing this factor and to methods for treating diseases or degenerative conditions of the connective tissue system with the factor or its compositions. In addition, the invention is directed to a method to obtain the factor from thyroid tissue and to methods to use the factor in vitro in the development of implant compositions or as a serum substitute in the growth of chondrocytes or fibroblasts. The invention is also directed to antibodies specifically immunoreactive with the factor, and to conjugates of the factor with label or other effector agents, and to the uses of these antibodies and conjugates.

MODES OF CARRYING OUT THE INVENTION

Figure 1:
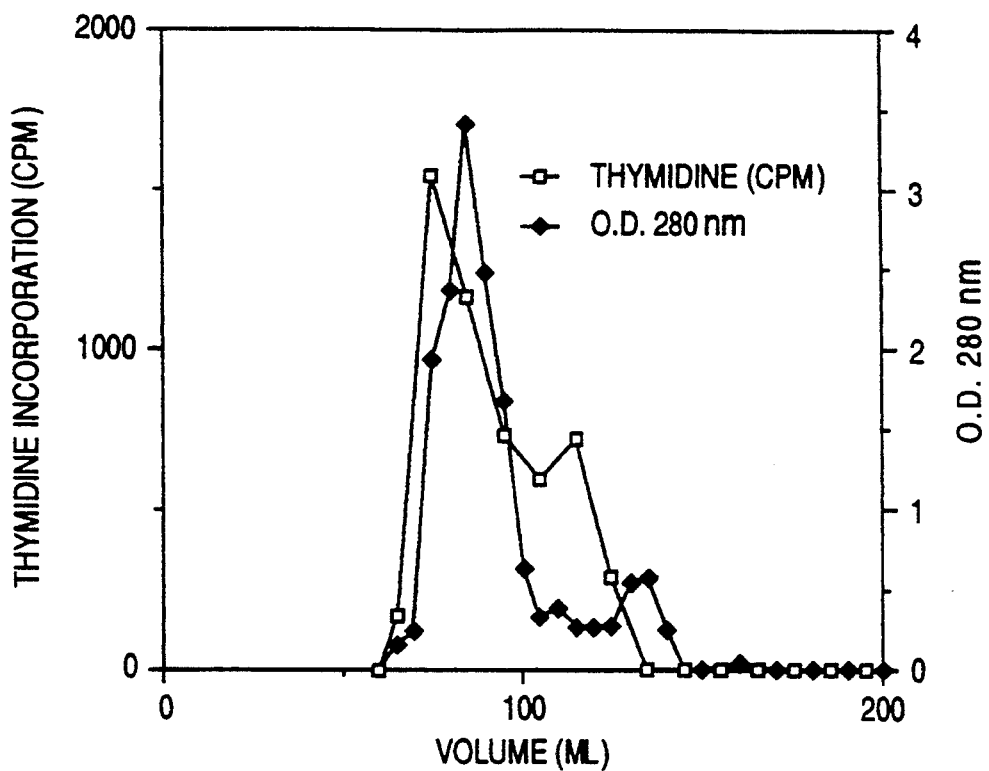
FIG. 1 shows the elution pattern for the factor of the invention from a Sephacryl S-300 column.

The inventive can be isolated from thyroid tissue and is provided as a high molecular weight complex of >500 kd. The complex can be at least partially dissociated by 8M urea into subunits which retain the activity of the complex, and are also of high molecular weight. As used herein, the "factor" (TDCSF) of the invention includes both the complex in undissociated form and the dissociated subunits, as described above. Both of these manifestations of the factor are capable of stimulating the growth of synovial fibroblasts adult articular chondrocytes under serum-free conditions.

The factor can be obtained from thyroid tissue by subjecting the 40–80% ammonium sulfate fraction from the tissue homogenate supernatant to chromatography on heparin-Sepharose. The factor elutes at approximately 0.5M NaCl and is dialyzed against DPBS containing 1 mM 2-ME before testing. Any samples to be stored are dialyzed against water containing 1 mM 2-ME and freeze-dried. The factor can be further purified by gel filtration. In the gel filtration treatment, the factor is excluded from a Sephacryl S-300 column with a molecular weight cutoff of $10^6$–$10^4$ daltons. The factor can be further purified, if desired, using native gel electrophoresis.

The isolated and purified factor has the following characteristics:

1. The complex form of the factor is at least partially dissociated by 8M urea into subunits which retain the characteristics of the complex listed below.
2. The factor is acidic—i.e., it does not bind to weak (carboxymethylcellulose) or strong (mono-S) cationic exchange columns at pH 7.2, but does bind to weak (DEAE cellulose) or strong (mono-Q) anion exchange columns at pH 7.2 under the following conditions: the candidate is applied to a column containing the anion or cation exchanger in the presence of 1/10 Dulbecco's phosphate-buffered saline (DPBS) at pH 7.2 in the presence of 1 mM β-mercaptoethanol (2-ME). The ion exchange resin has been preequilibrated in 1/10 DPBS. The presence or absence of the candidate in the flow-through volume is then assessed. The ion exchange resins can then be eluted in salt gradient to verify presence or absence of the candidate in the eluate.
3. The factor of the invention stimulates the growth of chondrocytes in the following assay.

Adult articular chondrocytes are prepared by collecting bovine cartilage from radiocarpal joints and dissociated in 20 ml Dulbecco's Modified Eagle's Medium (DMEM) containing gentamicin (50 μg/ml) and bacterial collagenase (CLS-II and CLS-IV), at a concentration of 0.5 mg/ml each (Kohatsu, N. D., et al., "Transactions of the 27th Annual Meeting of the Orthopedic Research Society" (1981), 6:214). The dissociated cells are collected by centrifugation at 450 g for 15 minutes and washed twice in DPBS and once in DMEM. Single cells are obtained by Nytex filtration and cell numbers determined by counting in a hemacytometer, and viability is assessed by Trypan Blue dye exclusion. After dilution in serum-free medium, the cells are dispersed in 16-mm plastic wells (24 wells/plate) at a density of $2 \times 10^5$ cells/cm$^2$ and incubated at 7% $CO_2$, 100% humidity, at 37° C. The medium consists of DMEM and Ham's F-12 medium mixed at a ratio of 1:1; the sulfate concentration of this mixture is 78.6 mg/l. Gentamicin (50 μg/ml), selenium ($2 \times 10^{-8}$M), and a lipid supplement (Bettger, W. J., et al., *Proc Natl Acad Sci USA* (1981) 78:5588–5592) were also added. These lipids are transferred to the medium as liposomes prepared just prior to use, as described in the Jones and Smith paper referenced above (*J Orthop Res* (1990) 8:227–233). Prior to use, the stock liposomes are diluted 1:1 in DMEM and the mixture is sonicated for 3 minutes at 4° C. under nitrogen and sterilized by ultrafiltration (0.22 μm). Culture dishes are treated with poly-D-lysine (0.1 mg/ml) before plating the cells under these serum-free conditions; polylysine is removed by repeated rinsing with sterile distilled water ($3 \times 1$ ml/well).

The foregoing culture medium is changed every three days and gentamicin (50 μg/ml) is maintained in all culture conditions. Each well contains 0.5 ml of medium.

In the assay itself, tritiated thymidine (methyl-3H-thymidine, 27.7 Ci/g) is added to the medium at 0.5 μCi/well, and the wells are incubated in the presence of the labeled thymidine for 72 hours at 37° C. The medium is then removed from each well and the cell layer gently rinsed twice with 1 ml DPBS to remove unincorporated thymidine. The cells are solubilized by addition of 0.5 ml 1N sodium hydroxide and heating at 60° C. for one hour. The solubilized samples are then counted.

4. The TDCSF of the invention stimulates the growth of synovial fibroblasts. The ability of the factor to stimulate the growth of synovial fibroblasts is assayed in the same manner as that set forth above for the assessment of stimulation of chondrocytes, except using synovial linings of the radiocarpal joints from 5–7-year-old dairy cows dissected under sterile conditions as the source of the cells. The synovial membrane is dissociated and the cells prepared and plated in the same manner as that set forth above for articular chondrocytes.
5. The factor of the invention has the following characteristics with respect to its ability to retain activity in the foregoing assays.
    a) Heating the factor at 60° C. for one hour does not destroy activity.
    b) Heating the factor to 100° C. for one hour does destroy activity.
    c) Treating the factor in the presence of 1 mM 2-mercaptoethanol (2-ME) in DPBS with trypsin (100 μg/ml) for 30 minutes at 25° C., whereupon the reaction is stopped with trypsin inhibitor (100 μg/ml) destroys activity.
    d) Treating the factor in the presence of 1 mM 2-mercaptoethanol (2-ME) in DPBS with 0.1M dithiothreitol (DTT) at 22° C. for 30 minutes does not destroy activity.
    e) Treating the factor in the presence of 1 mM 2-ME in DPBS in the presence of 1M acetic acid at 4° C. for 30 minutes destroys activity.

The factors in the latter three conditions are first dialyzed against DPBS with 1 mM 2-ME for 24 hours (using dialysis tubing of 1.2–2 kd) before testing for activity.

Using the foregoing criteria, the characteristics of the factors of the invention can be confirmed and verified.

Method of Preparation

The TDCSF of the invention is prepared from thyroid tissue of any vertebrate source, including human, bovine, porcine, avian or ovine.

A typical and convenient method begins with homogenization of human or bovine thyroid tissue to obtain a crude homogenate which is then centrifuged to obtain a supernatant. Centrifugation is at high g (about 30,000 g) for 30–60 minutes. The supernatant is then treated with a series of ammonium sulfate concentrations.

In a typical procedure, ammonium sulfate at 40% saturation at pH 7.2 is added and the precipitate removed. The ammonium sulfate concentration is then brought to 80% saturation at pH 7.2, and the precipitate is recovered. The recovered precipitate is then redissolved and dialyzed to remove the salts and subjected to chromatography on heparin-Sepharose.

The column is equilibrated with 0.5M NaCl, 25 mM Tris-HCl, pH 7.2, and 1 mM EDTA. The factor elutes from the column in 0.5M NaCl. The column can then be washed with a slightly higher concentration of salt, typically 0.65M NaCl.

This partially purified factor has the characteristics of TDCSF as set forth above. The activity-containing fractions are pooled and dialyzed thoroughly against water containing 1 mM 2-ME, then lyophilized and stored at −20° C. If they are to be tested directly for activity they are dialyzed against DPBS with 1 mM 2-ME. Prior to assay the factor is suspended in DPBS containing 1 mM 2-ME.

The factor may be stored in the presence of reducing agent (e.g., 1 mM 2-ME) for 1-2 years; activity is lost when the factor is stored even at −20° C. for more than 6 months in the absence of reducing agent.

In further purification, the dialyzed eluate from the heparin-Sepharose is subjected to Sephacryl S-300, which permits preparative separation of high molecular weight material from the remainder of the composition. The column is equilibrated with 1/10 DPBS containing 1 mM 2-ME. The factor elutes in the void volume when applied as described above, or when applied in the presence of 5M or 8M urea.

The factor may be further purified in its complex or dissociated form by subjecting it to gel electrophoresis under nondenaturing conditions.

Preparation of Antibodies

The partially purified factor eluted from the heparin-Sepharose column or the further purified materials resulting from gel filtration can be used as immunogens to produce antibodies specific for the TDCSF of the invention. These antibodies are useful in assessing the levels of naturally occurring TDCSF in biological fluids using standard immunoassay techniques. The antibodies are prepared using conventional immunization protocols by injecting the preparation, in the presence of adjuvant if needed, into suitable mammalian subjects such as rabbits, mice or sheep in repeated immunization, and measuring the titers in the serum of the injected host using standard ELISA or RIA assays. When high titer serum is obtained, the serum can be harvested as a source of antibodies for immunoassays. The antibodies or their specifically immunoreactive fragments, such as the Fab, Fab' or F(ab)'$_2$ can be used in these assays. The nature of the protocols for immunoassays using enzyme, radioactive, or fluorescent labels is well known in the art. In addition, antibody conjugated to solid support can be used to purify TDCSF by affinity chromatography.

In addition to the preparation of polyclonal antisera, monoclonal antibodies can be prepared to the TDCSF of the invention by harvesting the spleens, for example, of the immunized animals and immortalizing these cells by hybridization or viral infection. Immortalized cells secreting the desired antibodies are identified by subjecting the supernatants to immunoassays using the partially purified TDCSF of the invention as an antigen. Antibody-secreting colonies are then cultured in vitro or in ascites fluid.

Conjugates of the Factor

The factor may also be prepared as a conjugate with solid support, label or other effector molecule to take advantage of the ability of the factor to target chondrocytes and synovial fibroblasts. Label or an effector molecule which modifies the metabolism of the target cell can be coupled to the factor of the invention using standard coupling technology to deliver the label or effector to the target, or to bind target to solid support.

For example, uncontrolled growth of articular chondrocytes could be controlled by delivery of toxins to these cells using TDCSF conjugated to poisons such as ricin A or diphtheria toxin. In addition, cells whose metabolism is affected by the TDCSF of the invention can be labeled and localized using the factor coupled to radioactive or fluorescent label. In addition, the factor may be coupled to solid supports, and used as an affinity column for the purification of the antibodies prepared as described above or for purification and isolation of populations of cells containing receptors specifically reactive with TDCSF.

Utility and Administration

The factor of the invention is useful in stimulating the growth of chondrocytes and synovial fibroblasts both in vitro and in vivo.

First, as is apparent from the assay set forth above, the factor can be used as a serum substitute in the culture of these cells. Accordingly, both chondrocytes and synovial fibroblasts may be grown under serum-free conditions when the factor of the invention is added to the culture at concentrations on the order of 200 μg/ml culture medium (for the material purified approximately 5-fold from thyroid homogenate).

In addition, the factor of the invention is useful in developing cartilage implants for point repair in vitro. In such implants, chondrocytes are cultured to confluence using culture medium as described above on a preparative basis. A matrix may also be supplied to aid in the aggregation of the chondrocytes. The factor is supplied at concentrations comparable to those useful for in vitro culture in general, as described above.

The resulting implants can also be used in bone and tissue repair and additional amounts of the factor can be added to the implants in order to stimulate grafting to the surrounding tissue. Means to surgically implant such matrices into the skeletal system are understood in the art.

Further, the factors of the invention can be administered in standard pharmaceutical compositions either locally or systemically to stimulate cartilage repair and to maintain tissues under conditions of trauma or degenerative joint disease. Thus, subjects to which the factor of the invention could usefully be administered are those suffering from osteoporosis, bone fractures, degenerative diseases of the cartilage, or patients who have been supplied grafts which are coated with synovial fibroblasts or chondrocytes to aid in grafting. Preferably the TDCSF of the invention can be administered directly to affected tissue by lavage to the joints.

The following examples are intended to illustrate but not to limit the invention.

Example 1

Preparation and Purification of Chondrocyte-Stimulating Factor from Thyroid Tissue A modification of the method to isolate prostate epithelial cell growth factor from bovine brain (Crabb, J. W., et al., *Biochem Biophys Res Comm* (1986) 136:1155–1161; McKeehan, W. L., et al., *Anal Biochem* (1987) 164:563–569) was used. Briefly, bovine thyroid tissue (45 g) was homogenized in 450 ml of 0.15M NaCl (pH 7.0), containing 0.25 mM phenylmethylsulfonyl fluoride, 1 mM EDTA and 1 µg/ml of pepstatin, using a tissue blender and a Polytron tissue homogenizer (setting of 5, for 10 min, Model PT10, Brinkmann Instruments, Inc., Lucerne, Switzerland). The homogenate was centrifuged for 45 min at 30,000×g, and the supernatant was precipitated with ammonium sulfate at 40% and at 80% saturation, pH 7.2. The 40% precipitate was suspended in 100 ml of water, and the 80% precipitate was suspended in 36 ml of water. Both precipitates were dialyzed against 20 liters of water, with frequent changes over a 60-hour period. These dialyzed solutions were tested for ability to stimulate growth of articular chondrocytes as described above. The 80% precipitate showed activity, the 40% precipitate did not.

Portions of the homogenate and of the ammonium sulfate fraction precipitating between 40–80% saturation at pH 7.2 showed comparable activity in terms of total cpm calculated for the total sample, as shown in Table 1. About one-third of the total protein, but all the activity, was recovered in the 40–80% precipitate.

In further purification, 5 ml of the 80% dialyzed ammonium sulfate fraction (23.5 mg of protein) was added to a 1.5×22.0 cm heparin-Sepharose (Pharmacia) column equilibrated with 0.5M NaCl, 25 mM Tris-HCl (pH 7.2) and 1 mM EDTA. The column was washed with approximately two volumes (80 ml) of equilibration buffer. Fractions in the eluate which contained protein, as determined by UV absorbance (280 nm), were pooled. The column was then washed with 80 ml of a 0.65M NaCl, 25 mM Tris-HCl (pH 7.2) and 1 mM EDTA solution and 80 ml of a 2.0M NaCl, 25 mM Tris-HCl (pH 7.2) and 1 mM EDTA solution. Following both washes each eluate was pooled and the UV absorbances (280 nm) were measured and found to be below 0.10.

Each of the three eluates were dialyzed against 16 liters of $H_{20}$ with changes every 12 hours, for a period of 48 hours, then lyophilized overnight to dryness, resuspended in 50 ml of water, and stored at 20° C. Final protein determinations were made using the Bio-Rad Protein Assay (Bio-Rad Laboratories, Richmond, Calif.). For storage, the eluates should be freeze-dried in the presence of 1 mM 2-ME. Neither the 0.65M NaCl nor the 2.0M NaCl eluates contained activity in this assay; however, the fraction removed at 0.5M NaCl showed retention of total activity and most of the protein. These results are also shown in Table 1.

TABLE I

| Sample | Total Volume (ml) | Total Protein (mg) | Total Activity (cpm) | Total Activity (cpm/mg) | Fold Purified |
|---|---|---|---|---|---|
| Purification of Thyroid-Derived Chondrocyte Stimulation Activity | | | | | |
| Homogenate | 455 | 3767 | $24 \times 10^6$ | $6.4 \times 10^3$ | — |
| $(NH_4)_2SO_4$ | 36 | 1368 | $26 \times 10^6$ | $19 \times 10^3$ | 3 |
| 0.5M Eluant | 50 | 1350 | $33 \times 10^6$ | $24 \times 10^3$ | 4 |
| Sephacryl S-300 Fractionation | | | | | |
| No Urea | 5 | 10 | $44 \times 10^4$ | $44 \times 10^3$ | 7 |
| 5M Urea | 5 | 22 | $73 \times 10^4$ | $33 \times 10^3$ | 5 |
| 8M Urea | 3 | 6 | $28 \times 10^4$ | $46 \times 10^3$ | 7 |

The results of further purification on Sephacryl S-300 are discussed below.

Example 2

Characterization of the 0.5M Dialyzed Eluate

The dialyzed and lyophilized eluate could not be stored for more than six months at −20° C.; however, when 1 mM β-mercaptoethanol (2-ME) was added, the activity was stabilized so that it was retained over a two-year period.

A. The eluate was treated with 2M NaCl for 1 hour and size-fractionated with a Centricron-30 microconcentrator having a membrane pore size of 30 kd. All of the activity was shown to be in the retentate, thus indicating that the active factor is not an FGF heparin complex (this would have dissociated in 2M salt), which might prevent heparin-Sepharose binding.

B. The eluate failed to bind either weak or strong cation exchange columns, but did bind both weak and strong anion exchange columns when tested as set forth above. Treatment of the eluate on anion exchange resulted in dispersion of activity as a broad peak over gradient sodium chloride elution.

C. The eluate was also tested for its ability to stimulate labeled thymidine uptake by synovial fibro-blasts and shown to cause a 2.4-fold increase in uptake with the eluate used in excess. As a positive control, bFGF at 1 µg/ml produced an approximately equal increase in uptake.

D. There was a decrease in the activity in stimulating chondrocytes by the dialyzed eluate (404 cpm) when compared to the eluate alone wherein the resuspended factor had been diluted 1:1 with DPBS containing 1 mM 2-ME (903 cpm) but which was still significant as compared to control (174 cpm).

E. Further tests were conducted by combining 1 ml DPBS buffer containing 1 mM 2-ME with 1 ml of the dialyzed and resuspended 0.5M NaCl heparin-Sepharose eluate and testing the diluted solution.
  i) When 500 µl of this solution was adjusted to 0.1M DTT and maintained at 22° C. for 30 minutes, no decrease in activity was shown in the chondrocyte assay; indeed, the incorporation was slightly higher (526 cpm) than the dialyzed eluate.
  ii) An equal volume of the 1:1 dilution was adjusted to 1N acetic acid and maintained at 4° C. for 30 minutes, and then tested in the assay; the uptake of radioactivity when the treated eluate was tested was comparable to control (238 cpm).

iii) An addition 500 μl of the 1:1 dilution was treated with 100 μg/ml trypsin for 30 minutes at 25°C., and then stopped with 100 μg/ml trypsin inhibitor. This dropped the measured incorporation when the resultant was tested to 208 cpm, again insignificant.

The DTT-treated, HOAc-treated and trypsin-treated samples were dialyzed against 2 l of DPBS containing 1 mM 2-ME over 24 hours using a dialysis tubing of pore size 1.2-2 kd before testing in the assay.

F. Two 50 μl samples of the dialyzed and resuspended 0.5M NaCl eluate were heated at 60° C. and 100° C. respectively for 1 hour. The sample heated to 100° C. showed cpm uptake comparable to control; the 60° C. treated sample showed an uptake of approximately 400 cpm.

EXAMPLE 3

Further Purification of the 0.5M NaCl Eluate

The 0.5M NaCl eluate from the heparin-Sepharose column was further purified using Sephacryl S-300, which has a molecular weight cutoff of $10^4$–$10^6$ daltons. A 2.5×41.0 cm S-300 column was equilibrated with 1/10 DPBS containing 1 mM 2-ME. Four ml of the 0.5M NaCl heparin-Sepharose eluate was added to the column; the column was then washed in the equilibration buffer. In addition, this same S-300 column, equilibrated in 1/10 DPBS containing 1 mM 2-ME, was used to run aliquots of the 0.5M NaCl heparin-Sepharose eluate treated with 5M and 8M urea prior to column loading, taking into consideration secondary volume changes. The flow rate was 1 ml/min with all three columns.

Five ml fractions were collected for both the untreated and 5M urea-treated samples while 3 ml fractions were collected for the 8M urea-treated sample. Fractions were added directly to articular chondrocytes for assay as described above. Protein was determined by absorbance at 280 nm.

Figure 2:
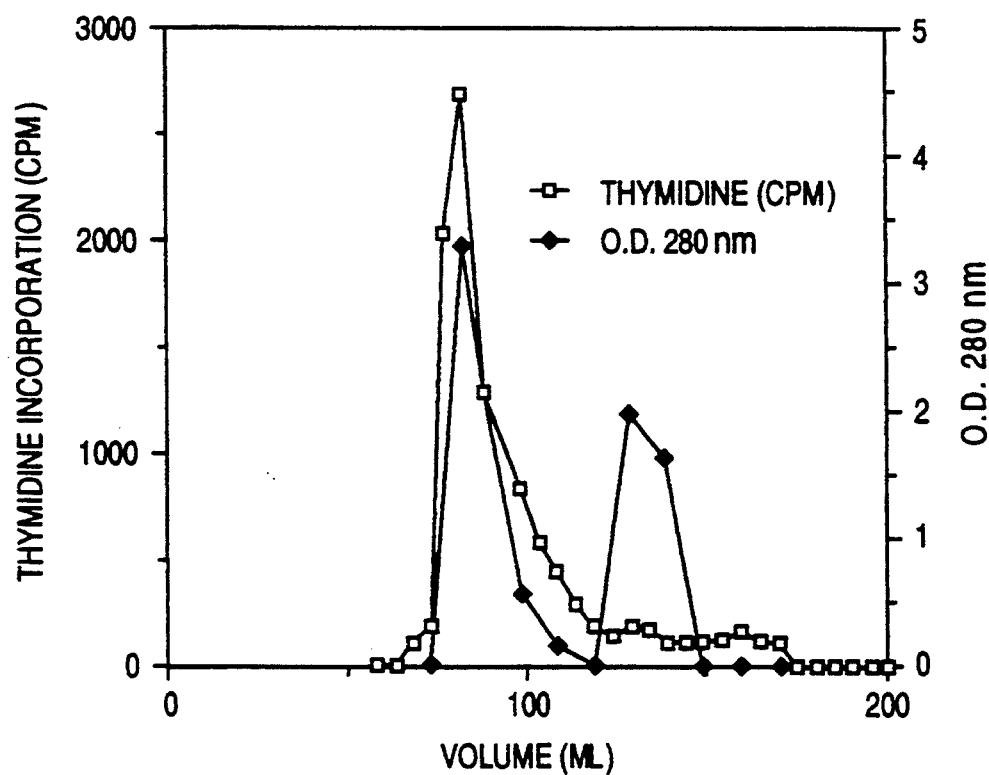
FIG. 2 shows an elution pattern analogous to that of FIG. 1, but with the inclusion of 5M urea.
Figure 3:
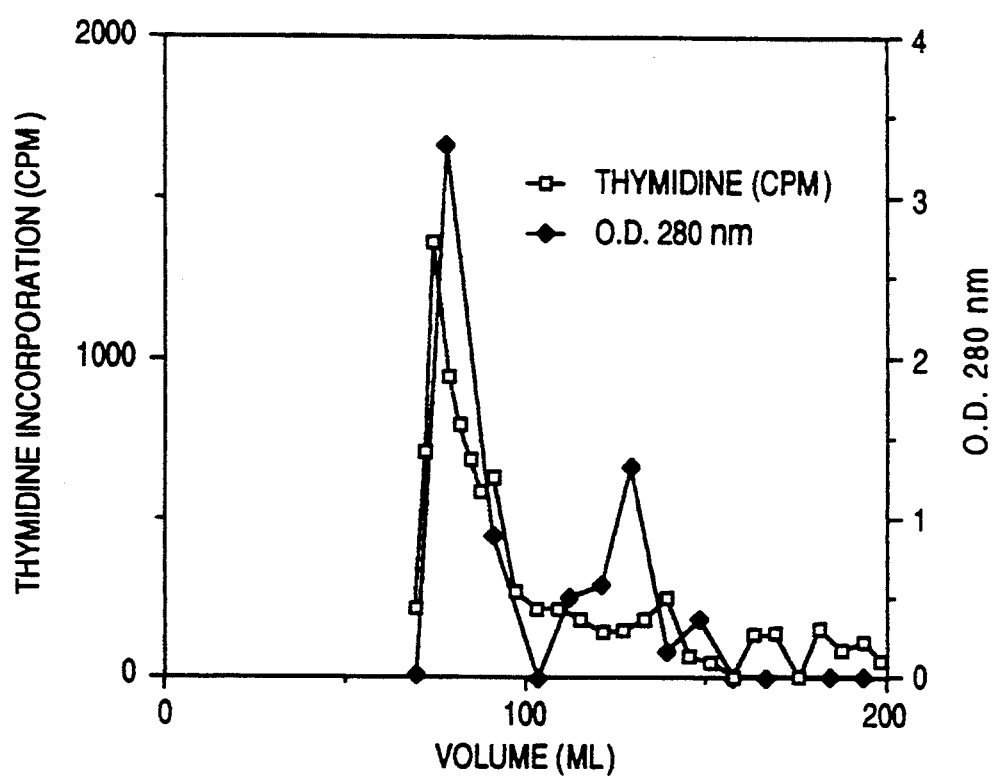
FIG. 3 shows an elution pattern analogous to that of FIGS. 1 and 2, but in the presence of 8M urea.

For the untreated eluate, the majority of stimulatory activity eluted at or near the Vo (65 ml) (FIG. 1). Adjustment of the eluate to 5M urea prior to loading on this column did not shift the activity or protein profiles (FIG. 2). Adjustment of the eluate to 8M urea provided the same initial peak at the Vo (FIG. 3), but having a 1.9-fold increase in specific activity (46,000 cpm/mg) when compared to the specific activity of the 0.5M NaCl heparin-Sepharose eluate (24,000 cpm/mg). Similar levels of specific activity were observed without treatment: (44,000 cpm/mg) or with 5M urea treatment (33,000 cpm/mg).

In all cases, a second peak of activity was observed at an elution volume of 115 ml; the second peak did not retain its stimulatory activity following storage at −20° C. even in the presence of 2-ME.

Table 1 above shows the effect of the Sephacryl S-300 fractionation on purification. Treatment with the Sephacryl column generally resulted in a modest increase in specific activity.

Example 4

Gel Electrophoresis

SDS polyacrylamide gel electrophoresis (SDS-PAGE) was performed according to the method of Laemmli, U.K., *Nature* (1970) 227:680–685, and non-denaturing discontinuous (native) gel electrophoresis was performed according to the method of Hames, B. D., et al., "Gel Electrophoresis of Proteins: A Practical Approach" (1981) IPI Press, Ltd., London and Washington, D.C., page 13. Approximately 5–15 μg of protein were run on each gel.

Figure 4:
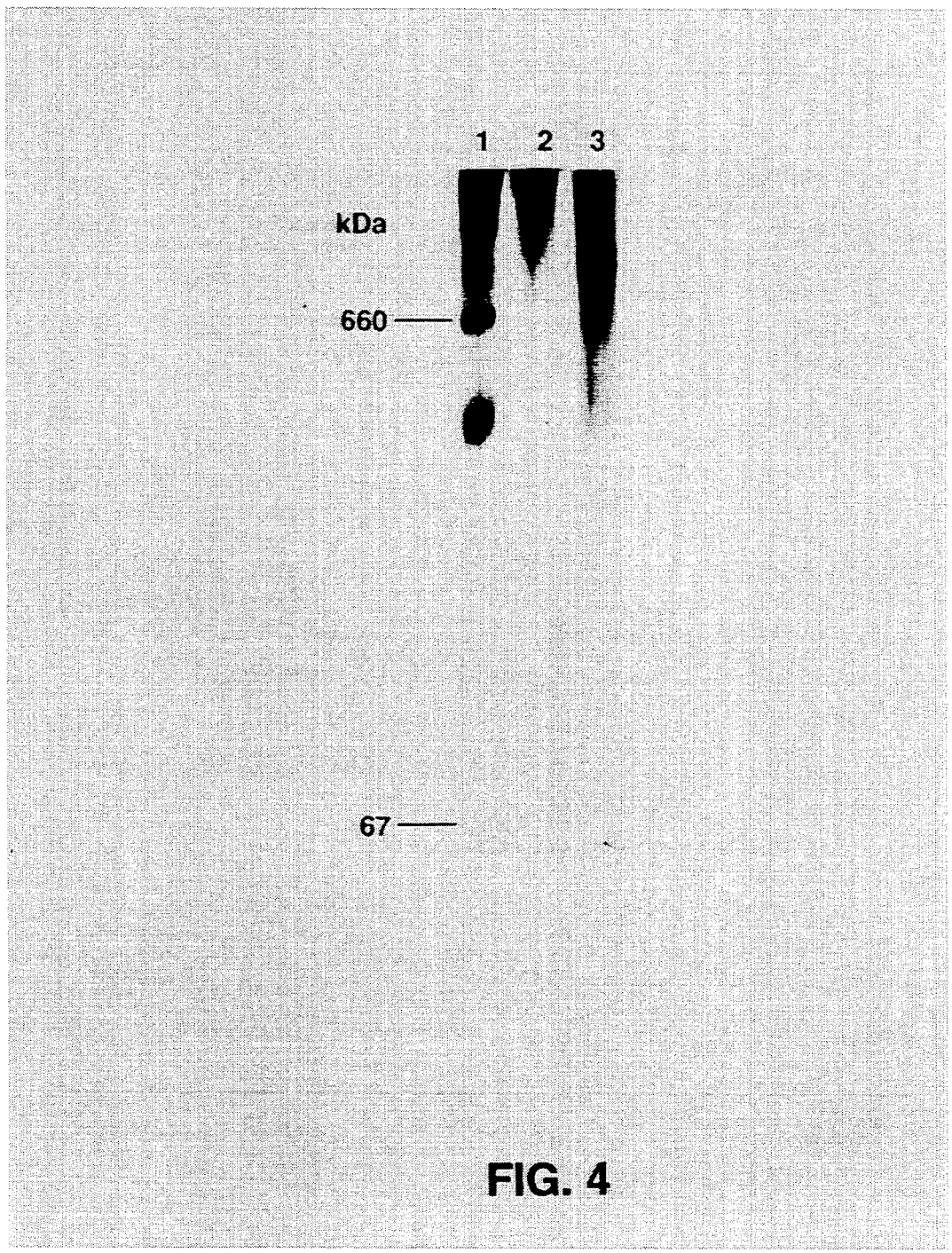
FIG. 4 shows the results of nonreducing native gel electrophoresis of the excluded volume shown in the elution patterns of FIGS. 1, 2 and 3.

The peaks from the Sephacryl S-300 columns containing the major activity were subjected to native PAGE on a 5% gel, and the gel was developed by Coomassie staining. The results are shown in FIG. 4.

Lane 1 is the fraction eluting at 75–79 ml from the column run without pretreating the eluate with urea. This developed gel shows a highly stained, high molecular weight region at the top of the gel and a band at 660 kd which is identified as thyroglobulin.

Lane 2 represents a comparable fraction (elution volume, 85–89 ml) from the 5M urea-treated eluate, and shows only the high molecular weight band.

Lane 3 shows the results of the corresponding eluate from the column wherein 8M urea treatment had been used; it shows a relative loss of intensity at the top of the gel in comparison to lane 2 and the production of two diffuse intensely stained regions. There are no lower molecular weight components on the gel. These results clearly demonstrate that the complex representing the factor of the invention undergoes at least partial dissociation, although there was no loss in activity, as set forth above.

EXAMPLE 5

Exclusion of Alternative Factors

As stated hereinabove, it is known that none of $T_3$, $T_4$ and calcitonin stimulate the growth of articular chondrocytes in the absence of serum; hence, these additional components of thyroid tissue cannot be responsible for the activity of the newly isolated factor. Thyroglobulin was tested directly in the chondrocyte assay described above and found to be inactive. Factors generally known which do have the ability to stimulate articular chondrocytes are also shown to be different from the factor of the invention.

As set forth above, fibroblast growth factor, both the acidic and basic forms, elute from heparin-Sepharose at a considerably higher salt concentration than does TDCSF. The elution of the factor of the invention at a lower concentration cannot be explained as the prevention of binding to the heparin-Sepharose by a prior complexation with heparin, as conditions designed to decouple this complex fail to liberate any factor from the preparation which behaves as FGF. Furthermore, it has been demonstrated by applicants that antibodies immunoreactive with FGF do not cross-react with the thyroid derived chondrocyte-stimulating factor of the invention using immunoblot techniques.

Insulin-like growth factor I (IGF-I) has a molecular weight of only 7.5 kd and is complexed to a binding protein of either 150 kd or 40 kd, both molecular weights much lower than that associated with the TDCSF of the invention. Furthermore, IGF-I is known to be stable to acid, unlike the TDCSF. IGF-II is reported to be similar to IGF-I.

Epidermal growth factor (EGF) also is of low molecular weight and requires intramolecular disulfide bonds for activity. Hence, EGF is inactive in the presence of disulfide reducing agents, unlike the factor of the invention. Furthermore, EGF is known to be stable to acids. Antibodies prepared against EGF do not cross-react with the TDCSF; in addition, anti-EGF does not inhibit the stimulatory activity of the thyroid-derived factor described herein.

TGF-$\beta$ is also a low molecular weight molecule which is, unlike the present factor, stable to acid. TGF-$\beta$ also requires disulfide linkages for activity and is unstable to reducing agents capable of reducing the disulfide to sulfhydryl groups.

Finally, PDGF can be distinguished from the thyroid-derived factor of the invention by virtue of its inactivity in the presence of disulfide reducing agents.

We claim:

1. A method to develop cartilage implants in vitro, which method comprises
    (a) treating a culture of adult chondrocytes with thyroid-derived chondrocyte stimulating factor (TDCSF) in isolated and purified form, which TDCSF is obtainable from mammalian thyroid tissue by a process which comprises
    homogenizing thyroid tissue;
    removing particles from the homogenate to obtain a particle-free first supernatant;
    treating the supernatant with ammonium sulfate at 40% saturation to obtain a first precipitate and a second supernatant;
    recovering the second supernatant;
    treating the second supernatant with 80% saturation of ammonium sulfate, pH 7.2, to obtain a second precipitate and a third supernatant;
    redissolving said second precipitate and removing ammonium sulfate therefrom;
    treating said redissolved and desalted second precipitate with heparin-Sepharose under conditions wherein said TDCSF is adsorbed to the heparin-Sepharose;
    recovering the heparin-Sepharose containing the adsorbed TDCSF;
    eluting a multiplicity of fractions from said heparin-Sepharose column;
    recovering a fraction containing TDCSF as shown by the activity of stimulating the growth of adult chondrocytes and synovial fibroblasts under serum-free conditions;
    applying said fraction to a Sephacryl S-300 column under conditions wherein said activity is present in the flow-through volume of said Sephacryl column;
    recovering said flow-through volume;
    subjecting said flow-through volume to polyacrylamide gel electrophoresis under nondenaturing conditions to obtain a multiplicity of fractions; and
    recovering at least one fraction from said gel which contains said TDCSF
    to thus obtain said isolated and purified TDCSF;
    wherein said conditions under which said fraction is subjected to in said Sephacryl S-300 column in order to retain said activity in said flow-through volume include equilibrating with 1/10 DPBS containing 1 mM $\beta$-mercaptoethanol;
    wherein said TDCSF stimulates the growth of adult chondrocytes and synovial fibroblasts under serum-free conditions;
    wherein said TDCSF is acidic, is sensitive to trypsin digestion, is inactivated by treating with 1M acetic acid for 1 hour at 4° C. and by treating at 100° C. for one hour, but is not inactivated by treating at 60° C. for one hour;
    wherein said TDCSF elutes from heparin-Sepharose at 0.5M NaCl;
    wherein said TDCSF is a proteinaceous complex or active subunit thereof; said complex or said active subunits having a molecular weight greater than 500 kd and said complex remaining active after treatment with and being at least partially dissociable into active subunits by 8M urea; and
    wherein said TDCSF is stabilized in the presence of reagents capable of reducing disulfide linkages
    under conditions wherein said chondrocytes are aggregated to provide said implant; and
    (b) recovering the implant from the culture.

2. The method of claim 1 wherein the culture further includes a matrix for the support of the implant.

* * * * *